(12) United States Patent
Himmelsbach et al.

(10) Patent No.: US 6,274,205 B1
(45) Date of Patent: Aug. 14, 2001

(54) PROCESS FOR THE AT LEAST PARTIAL, DIRECT COATING OF AN EXTENSIBLE BACKING MATERIAL WITH A PRESSURE-SENSITIVE ADHESIVE COMPOSITION

(75) Inventors: Peter Himmelsbach, Buxtehude; Peter Jauchen; Klaus Keite-Telgenbüscher, both of Hamburg; Matthias Lehder, Buchholz, all of (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/205,345

(22) Filed: Dec. 4, 1998

(30) Foreign Application Priority Data

Dec. 13, 1997 (DE) ................................. 197 55 437

(51) Int. Cl.7 ................................. H01F 1/00; B05D 5/10
(52) U.S. Cl. .................... 427/547; 427/191; 427/195; 427/208.4; 427/208.6; 427/307; 427/322; 427/327; 427/598

(58) Field of Search ............................. 427/208.4, 208.6, 427/488, 489, 490, 598, 547, 322, 574, 307, 578, 327, 569, 191, 195

(56) References Cited

U.S. PATENT DOCUMENTS 3,102,046 * 8/1963 Bushey .
4,199,649 * 4/1980 Yundt .
5,662,758 * 9/1997 Hamilton et al. .

\* cited by examiner

*Primary Examiner*—Bernard Pianalto
(74) *Attorney, Agent, or Firm*—Norris McLaughlin & Marcus

(57) ABSTRACT

Process for the at least partial direct coating of an extensible backing material with a pressure-sensitive adhesive composition, the backing material being guided by a transporting apparatus against a coating apparatus in such a way that the coating apparatus applies the pressure-sensitive adhesive composition to the backing material, characterized in that the coating apparatus is abhesively treated.

13 Claims, No Drawings

PROCESS FOR THE AT LEAST PARTIAL, DIRECT COATING OF AN EXTENSIBLE BACKING MATERIAL WITH A PRESSURE-SENSITIVE ADHESIVE COMPOSITION

The invention relates to a process for the at least partial, direct coating of an extensible backing material with a pressure-sensitive adhesive composition, the backing material being guided by a transporting apparatus against a coating apparatus in such a way that the latter applies the pressure-sensitive adhesive composition to the backing material.

The use of extensible materials as backings having elastic or plastically formable properties is known in both industry and medicine. They are used in a wide variety of areas—inter alia, as base materials in the production of plasters and adhesive dressings.

The term "plastically or elastically deformable" is intended to denote the extensibility of a material. In accordance with this a material is extensible if under a load of 10 N/cm it exhibits an increase in length of at least 20%.

It is also known that the extensible backing materials can be coated with various adhesive systems. In general, coating can be performed over the whole area or else partially. With medical, self-adhesively treated backing materials it is found in this case that, given appropriately porous backing materials, the result is a highly air-permeable and water-vapour-permeable film which in general can also be detached fairly easily again after it has been bonded to the skin of the patient.

Half-tone printing is widespread as a process for producing such partially coated backing materials—especially screen, gravure or flexographic printing. It is also known that the self-adhesive treatment can also be applied to more than one side, in the case, for example, of use as fixings.

The adhesive compositions which can be used are, in principle, solvent-based or dispersion-based systems, or else 100% systems. When processing the 100% systems it is an advantage that there is no need to remove the solvents or dispersion auxiliaries. This increases the productivity and at the same time reduces the expenditure on machinery and the energy costs.

Elastic or plastically formable backing materials can generally be coated directly or indirectly. In the case of indirect coating, a preferably rigid or fairly nonelastic auxiliary support is coated first of all and then the adhesive composition is transferred in a laminating process to the elastic or plastically formable backing. For indirect coating it has been found advantageous that in this case the backing material can be laminated essentially without deformation and prior loading, so leading to the extensive retention of shape and of textile technological features such as basis weight, maximum tensile strength, extension under maximum tension, and hysteresis extension.

The disadvantage of indirect coating lies in the relatively poor anchorage of the adhesive composition to the elastic or plastically deformable backing. Here it is found that, especially in the case of temperature-sensitive backing materials, thermal lamination is impossible or largely unsuccessful. In the case of thick, porous backing materials, lamination may be accompanied by the adhesive film being pressed completely into the backing, with the consequence of a drastic deterioration in both the bonding properties and the elasticity.

Direct coating, although it permits a much improved anchorage of the adhesive composition, entails greater stress on the backing both thermally and mechanically. Especially in the case of partial application of adhesive composition to an at least partially elastically or plastically formable backing material it is found that this material, although the backing is placed unstressed and without deformation into the coating unit, is stressed in some cases to such an extent that there is an irreparable change in its properties. This is a consequence of the fact that the adhesive system adheres to the coating system with a system-dependent force.

In order to separate the self-adhesively treated backing from this coating unit, it is necessary to exert a force on the backing, as a result of which the latter experiences an impairment of its properties, especially its elasticity and basis weight.

The object of the invention was to develop a direct coating process which makes it possible to coat an extensible backing material at least partially with a pressure-sensitive adhesive composition without altering the properties of the backing.

This object is achieved by a process as described in more detail in Claim 1. The subclaims represent advantageous embodiments.

Accordingly, in the process of the invention for the at least partial, direct coating of an extensible backing material with a pressure-sensitive adhesive composition, the backing material is guided by a transporting apparatus against a coating apparatus in such a way that the latter applies the pressure-sensitive adhesive composition to the backing material, with the coating apparatus being abhesively treated, so that coating is not accompanied by any change in the properties of the backing.

In one advantageous embodiment of the process, the backing material is coated over its whole area.

The abhesive (anti-adhesive) treatment consists preferably of silicones or fluorine compounds, or plasma-coated release systems.

Also preferably, the abhesive is applied with a weight per unit area of from 0.01 to 350 g/m$^2$, more preferably 0.1 to 10 g/m$^2$.

In a particularly preferred embodiment the transporting apparatus consists of a pressure roller and the coating apparatus of a rotating, seamless, drum-shaped, perforated and abhesively treated cylindrical screen which is fed via a nozzle with the pressure-sensitive adhesive composition, the pressure-sensitive adhesive composition being applied by way of a nozzle lip through the cylindrical screen and onto the backing material that is conveyed past it.

The pressure roller can consist preferably of metal, ceramic or plastic. It can be generally plastic, elastic or rigid in configuration.

Furthermore, there can be adhesion devices or holding devices present on the transporting apparatus.

The holding apparatuses consist in particular of needles which project from the transporting apparatus and engage in the backing material, and which have a length greater than 10 µm, preferably between 30 and 5000 µm and, with particular preference, between 35 and 1000 µm.

Moreover, the needles can at least in part be mobile on the surface of the transporting apparatus.

A combination that has been found to be very advantageous is that of thermal screen printing with needles in the counterpressure roller. Depending on the target application it is possible to equip the counterpressure roller such that the roughness and/or the needles are present uniformly, randomly distributed or in a defined geometric pattern on the roller surface. The geometric form and extent of the adhesion elements are also adapted to the backing. The configuration of needle orientation has also been found advantageous.

For specific uses, the angle of needle orientation can be between 10° and 170° to the tangent to the surface of the roller in the coating direction and perpendicular to the coating direction. In addition, the angle of needle orientation can, for specific uses, be between 10° and 170° to the web direction.

The needles can, moreover, be designed at least in part to be mobile, so that their orientation and/or size may change during one revolution of the counterpressure roller as a result, for example, of exposure to a magnetic field or of eccentric constructions.

In addition, the surface of the counterpressure roller and/or of the adhesion elements can be pretreated both physically and chemically. By way of example, mention may be made here of siliconization and of Teflonization. A static or else antistatic treatment may give rise to applications-related advantages.

Techniques for applying such release coverings are adequately described in the technical literature, with examples being dipping, brushing, spraying and printing. The release coverings can be cured both physically and chemically. Chemically curing systems have been found advantageous for the processing of hotmelt adhesive compositions.

A further advantageous embodiment of the holding apparatuses on the transporting apparatus consists in the use of very rough surfaces i.e. in a generally unordered arrangement of geometries suitable for engagement in the extensible backing.

The roughened surface can be formed from applied particles of hard material and/or of a metal, ceramic or plastic surface roughened by the shaping procedure or by means of mechanical, physical or chemical treatment.

Mention may be made here by way of example of coatings of corundum or similar hard materials, which have a sandpaper-like surface. Alternatively, metal surfaces roughened by etching or other techniques are appropriate.

The peak-to-valley roughness of the surface is advantageously between 30 and 5000 $\mu$m.

An alternative option is the use of holding apparatuses which are active through forces of adhesion; for example, the use of a self-adhesive composition whose adhesive force is tailored to the system as a whole.

For appropriate backing materials, electromagnetic fields are also suitable for applying the holding forces.

The process will be described by way of example on the principle of thermal screen printing, without wishing thereby to restrict the invention unnecessarily.

The principle of thermal screen printing consists in the use of a rotating, heated, seamless, drum-shaped, perforated, cylindrical screen which is fed via a nozzle with the pressure-sensitive adhesive composition. A specially shaped nozzle lip (circular- or square-section coating bar) presses the self-adhesive composition, which is fed in via a channel, through the perforation of the screen wall and onto the backing web that is conveyed past it. This backing web is guided by means of a counterpressure roller against the external jacket of the heated screen drum at a rate which corresponds to the peripheral speed of the rotating screen drum.

The release treatment of the mechanically equipped counterpressure roller can be effected by a very wide variety of techniques. Common anti-adhesive coatings are made by way of treatments with silicone or fluoropolymer coatings. The most common polymer systems are condensation or addition-crosslinking solutions. New techniques such as the plasma coating system supplement the range of options.

This counterpressure roller is equipped with a needled surface such that it is able to exert a force which is oriented in a directionally dependent manner in such a way that it is slightly greater than the force of adhesion of the cooling adhesive melt to the screen drum surface.

The backing web is removed from the counterpressure roller by means of a perpendicularly directed air stream.

The formation of the domes of adhesive remains unaffected by the above-mentioned apparatuses and, in the case of the production of the partially coated elastic or plastically deformable backing material, takes place in accordance with the following mechanism:

The pressure of the nozzle coating bar conveys the pressure-sensitive adhesive composition through the screen perforation onto the backing material. The size of the domes formed is predetermined by the diameter of the screen perforation. The screen is lifted from the backing in accordance with the rate of transportation of the backing web (rotary speed of the screen drum). As a consequence of the high adhesion of the pressure-sensitive adhesive composition and of the internal cohesion of the hotmelt, the limited supply of pressure-sensitive adhesive composition in the perforations is drawn in sharp definition from the base of the domes that is already adhering to the backing and is conveyed onto the backing by the pressure of the coating bar.

Following the end of this transportation, the more or less highly curved surface of the dome is formed over the predefined base area in dependence on the rheology of the pressure-sensitive adhesive composition. The height-to-base ratio of the dome depends on the ratio of the perforation diameter to the wall thickness of the screen drum and on the physical properties (flow behaviour, surface tension and contact angle with the backing material) of the self-adhesive composition.

The above-described mechanism of formation of the domes requires, preferentially, backing materials that are absorbent or at least wettable by pressure-sensitive adhesive composition.

Non-wetting backing surfaces must be pretreated by chemical or physical methods. This can be effected by means of additional measures such as corona discharge or by coating with substances which improve wetting.

Using the printing technique indicated it is possible to lay down the size and shape of the domes in a defined manner. The adhesive force values which are relevant for use, and which determine the quality of the products formed, are within very narrow tolerances provided that coating is carried out correctly. The base diameter of the domes can be chosen to be from 10 to 5000 $\mu$m, the height of the domes from 20 to about 2000 $\mu$m, preferably from 50 to 1000 $\mu$m, the low-diameter range being intended for smooth backings and the range of greater diameter and greater dome height being intended for rough or highly porous backing materials.

The positioning of the domes on the backing is laid down in a defined manner by the widely variable geometry of the applicator unit, for example the gravure or screen geometry. With the aid of the parameters indicated it is possible, by way of adjustable variables, to establish with very great precision the desired profile of properties of the coating, harmonized with the various backing materials and applications.

The backing material is preferably coated at a rate of more than 2 m/min, preferably from 20 to 100 m/min, the chosen coating temperature being greater than the softening temperature.

EXAMPLE 1

Elastic medical bandages were coated directly.

By means of the disclosed invention it was possible to omit the auxiliary support for indirect coating and to omit the environmentally compatible recovery of the solvent, which is costly and entails high mechanical expenditure. The bandage was coated by thermal screen printing with 160 g/m$^2$ of an adhesive composition based on a block copolymer.

The block copolymer was a styrene-ethylene-butylene-styrene block copolymer to which paraffinic hydrocarbon waxes had been added. The proportion was one part of polymer to one part of paraffinic hydrocarbon. 10% of polystyrene resin (Amoco 18240) was added to this mixture. The adhesive contained one per cent of Irganox, an anti-ageing agent (n-octadecyl β-(3,5-di-t-butyl-4-hydroxyphenyl)propionate), and further hydrocarbon resins and fatty acid esters, which were present only in small amounts in the overall adhesive. The softening point of this adhesive composition was 100°C. (DIN 52011) and its glass transition temperature, determined by the abovementioned method, was −60° C.

The following characteristic values for the elastic and plastic properties of the bandage were measured:

|  | Conventional direct thermal screen printing | Novel direct thermal screen printing |
| --- | --- | --- |
| Extension at 10 N/cm | 45% | 87% |
| Plastic deformation at 10 N/cm | 25% | 25% |

The high level of application of the composition was achieved using a 14-mesh screen. The use of the large coating dots made it possible to obtain good adhesion to the backing, and clean cutting. In accordance with the invention, the adhesive composition was skin-compatible and showed good adhesion to the skin and to the reverse of the backing.

The abhesive coating employed was a 1.8% strength, thermally crosslinking silicone solution. The reaction time was 10 minutes at 120° C.; the chosen coating technique was the spray method.

The bandage produced in this way, even in a multi-ply dressing, was permeable to air (more than 15 cm$^3$/(cm$^2$*s)) and permeable to water vapour (more than 1500 g/(m$^2$*24h)).

The elastic adhesive bandage was used for compression, support and relief dressings, where the high initial and long-term adhesive force and the shear strength were advantageous. The shapeability and sensation obtained by the user were improved as a result of the partial application of the adhesive composition.

What is claimed is:

1. Process for the at least partial, direct coating of an extensible backing material with a pressure-sensitive adhesive composition, the backing material being guided by a pressure roller against a rotating, seamless, drum-shaped, perforated and abhesively treated cylindrical screen which is fed via a nozzle with the pressure-sensitive adhesive composition, the pressure-sensitive adhesive composition being applied by way of a nozzle lip through the cylindrical screen and onto the backing material that is conveyed past it.

2. Process according to claim 1, wherein the backing material is coated over its whole area.

3. Process according to claim 1, wherein the abhesive (anti-adhesive) treatrment comprises the application of silicones, fluorine compounds, or plasma-coated release systems to the cylindrical screen.

4. Process according to claim 1, wherein the abhesive is applied with a weight per unit area of from 0.01 to 350 g/m$^2$, preferably 0.1 to 10 g/m$^2$.

5. Process according to claim 1, wherein there are adhesion devices or holding devices present on the pressure roller so that coating is not accompanied by any change in the properties of the backing.

6. Process according to claim 5, wherein the holding devices are electromagnetic fields whose forces act on the backing material.

7. Process according to claim 5, wherein the holding devices are needles which project from the pressure roller and engage in the backing material.

8. Process according to claim 7, wherein the needles have a length greater than 10 μm.

9. Process according to claim 7, wherein the needles are at least in part mobile on the surface of the pressure roller.

10. Process according to claim 5, wherein the holding devices are a roughened surface whose roughness geometries engage in the backing material.

11. Process according to claim 10, wherein the peak-to-valley roughness of the surface is between 30 and 5000 μm.

12. Process according to claim 10, wherein the roughened surface is formed by applied particles of hard material, a metal, ceramic or plastic surface roughened by a shaping procedure or by means of mechanical, physical or chemical treatment, or a combination of said particles and said roughened surface.

13. Process according to claim 5, wherein the adhesion device is a self-adhesive surface whose forces of adhesion act on the backing material.

* * * * *